United States Patent
Kunz et al.

Patent Number: 5,849,041
Date of Patent: Dec. 15, 1998

[54] OXIDATION HAIR DYE COMPOSITION AND METHOD OF DYEING HAIR USING SAME

[75] Inventors: Manuela Kunz, Marly; Dominique Le Cruer, Bonnefontaine, both of Switzerland

[73] Assignee: Wella Aktiengesellschaft, Darmstadt, Germany

[21] Appl. No.: 811,614

[22] Filed: Mar. 5, 1997

[30] Foreign Application Priority Data

Mar. 16, 1996 [DE] Germany ............ 196 10 392.4

[51] Int. Cl.$^6$ .................................... A61K 7/13
[52] U.S. Cl. .................. 8/408; 8/401; 8/405; 8/406; 424/94.4
[58] Field of Search ................ 424/70.1, 94.4; 8/401, 405, 406; 132/202, 208

[56] References Cited

U.S. PATENT DOCUMENTS

| | | | |
|---|---|---|---|
| 3,251,742 | 5/1966 | Soloway . | |
| 3,893,803 | 7/1975 | Kaiser . | |
| 3,957,424 | 5/1976 | Zeffren . | |
| 4,961,925 | 10/1990 | Tsujino et al. | 424/70.2 |
| 5,167,669 | 12/1992 | Grollier | 8/405 |
| 5,200,175 | 4/1993 | Tabata et al. | 424/70.51 |
| 5,480,460 | 1/1996 | Muraoka | 8/416 |
| 5,538,517 | 7/1996 | Samain . | |
| 5,628,799 | 5/1997 | Wenke et al. | 8/407 |

FOREIGN PATENT DOCUMENTS

| | | |
|---|---|---|
| 0310675 | 4/1989 | European Pat. Off. . |
| 310675 | 4/1989 | European Pat. Off. . |
| 0548620 Ai | 6/1993 | European Pat. Off. . |
| 0310675B1 | 1/1994 | European Pat. Off. . |
| WO94/00100 | 1/1994 | WIPO . |
| WO9400100 | 1/1994 | WIPO . |

OTHER PUBLICATIONS

Database WPI an 78–33901A Derwent Pub. Mar. 27, 1978.

Primary Examiner—Robert H. Harrison
Attorney, Agent, or Firm—Michael J. Striker

[57] ABSTRACT

The composition for oxidative dyeing of keratin fibers has a pH of from 6 to 9.5 and contains a developer/coupler combination, an oxygen-oxidoreductase/substrate system and a peroxidase. The coupler substance includes a substituted m-phenylenediamine of formula I

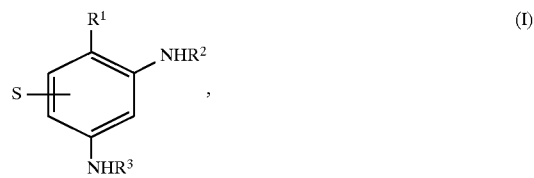

wherein $R^1$ is a $C_1$- to $C_6$-alkoxy group, an unsubstituted alkyl group having from one to six carbon atoms, a $C_1$- to $C_6$-alkyl group substituted with a hydroxy group, a halogen atom or a $C_1$- to $C_6$-alkoxy group; and $R^2$, $R^3$ are each, independently of each other, a hydrogen atom, another unsubstituted $C_1$- to $C_6$-alkyl group, an unsubstituted $C_1$- to $C_6$-ether group having at most two oxygen atoms, another $C_1$- to $C_6$-alkyl group substituted with a hydroxy group, a halogen atom or a $C_1$- to $C_6$-alkoxy group substituent or an ether group substituted with a hydroxy group, a halogen atom or a $C_1$- to $C_6$-alkoxy group, and S represents a hydrogen atom or a further alkyl group having from one to six carbon atoms, or a physiologically compatible salt of the m-phenylenediamine of the formula (I).

14 Claims, No Drawings

OXIDATION HAIR DYE COMPOSITION AND METHOD OF DYEING HAIR USING SAME

BACKGROUND OF THE INVENTION

The present invention relates to an oxidation hair dye composition for oxidative dyeing of keratin fibers based on a developer/coupler substance combination and an enzymatic oxidation system and method of dyeing keratin fibers using it.

Oxidation hair dye compositions have attained a substantial importance in the field of dyeing keratin fibers. The dyeing with oxidation hair dye compositions results from a reaction of certain developer substances with certain coupler substances in the presence of a suitable oxidizing agent. Developer and coupler substances are usually mixed first prior to use with an oxidizing agent. The ready-to-use hair dyeing mixture obtained in this way is then applied to the keratin fibers to be dyed. Since excess hair dyeing mixture should not be stored, the remaining residual hair dyeing mixture must be thrown out. Normally a 2 to 9% hydrogen peroxide preparation is used. The use of this type of comparatively high oxidizing agent concentration, can, particular with bleached or permanently waved hair, however lead to damaged hair.

To obtain a satisfactory hair dyeing result which survives several hair washes, the hair dyeing normally takes place in a comparatively highly alkaline pH range (pH>9), whereby additional damage of the hair is caused.

Using enzymes as biocatalysts the oxidation of the developer substance/coupler substance can occur with or without the use of hydrogen peroxide so that a pH value in the weakly acidic to weakly alkaline ranges is sufficient for the hair dyeing. In this way the hair can be better protected.

One disadvantage of this type of enzymatically catalyzed oxidative hair dyeing is the reduced intensity and maintainability of the hair colors obtained in the hair dyeing in contrast to the conventional oxidative hair dyeing.

Oxidation hair dye compositions based on an enzymatic oxidation are known and described, for example, in International Patent Application WO 94/00 100 and European Patent Application EP-OS 0 310 675. The compositions described in these disclosures have a series of disadvantages. Thus the indole or indoline characterized as dye precursors and multiple process steps are required in the dyeing process known from International Patent Application WO 94/00 100, while no satisfactory hair dyeing result can be obtained with the hair dye compositions described in European Patent application EP-OS 0 310 675 which are particularly poor for producing intense dark shades.

SUMMARY OF THE INVENTION

It is an object of the present invention to make available oxidative hair dyeing compositions and methods of dyeing hair for keratin fiber, especially human hair, which provide intense colors, especially in the natural color shade ranges, for the dyed hair which are resistant to washing in a simple way and which provides the greatest possible protection for the keratin fibers.

According to the invention, the composition for oxidative dyeing of keratin fibers, especially hairs, has a pH of from 6 to 9.5 and contains a combination of developer substance and coupler substance, an oxygen-oxido-reductase/substrate system and a peroxidase, wherein the coupler substance comprises a m-phenylenediamine of formula I or its physiologically compatible salt,

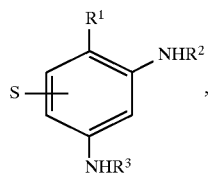

wherein $R^1$ represents an alkoxy group having from one to six carbon atoms, an unsubstituted alkyl group having from one to six carbon atoms or a substituted alkyl group having from one to six carbon atoms and one or more hydroxy group, halogen atom or $C_1$- to $C_6$-alkoxy group substituents; $R^2$, $R^3$ represent, independently of each other, hydrogen, an unsubstituted alkyl group having from one to six carbon atoms or a substituted alkyl group having from one to six carbon atoms and one or more hydroxy group, halogen atoms or $C_1$- to $C_6$-alkoxy group substituents, wherein the alkyl group may be interrupted by a maximum of 2 oxygen atoms to form an ether group; and S represents a hydrogen atom or an alkyl group having from one to six carbon atoms.

The hair dye composition according to the invention attains the objects of the invention in an outstanding manner.

The following compounds are among the compounds of formula I which are particularly preferred:
4-(2'-hydroxyethyl)-1,3-diaminobenzene dihydrochloride,
4-propyl-1,3-diaminobenzene dihydrochloride,
4-(2',2',2'-trifluoroethoxy)-1,3-diaminobenzene,
4-(2'-hydroxyethoxy)-1,3-diaminobenzene dihydrochloride,
2-amino-4-methoxyethylamino anisole,
2-amino-4-hydroxypropylamino-anisole dihydrochloride,
2-amino-4-(2',2',2¹'-trifluoroethyl)amino anisole,
4-amino-2-ethylamino-anisole dihydrochloride,
4-amino-2-(2',2',2'-trifluoroethyl)amino anisole and
2-amino-4-(2'-hydroxyethyl)amino anisole sulfate.

Aromatic amines, diaminophenoles or aminophenoles, whose amino- or hydroxy groups are in ortho- or para-position in relation to each other, for example 1,4-diaminobenzene, 2,5-diaminotoluene, 2,5-diaminophenyl-ethanol, o-aminophenol or 4-amino-m-cresol, are preferred as the developer substance. Also mixtures of these developer compounds may be used as the developer substance.

Although the compounds of formula (I) are preferred as coupler substances, it is understandably possible to use coupler substances of the formula (I) together with known coupler substances, such as, e.g., aromatic m-diamines, m-aminophenols, polyphenols or naphthols, especially 1,3-diaminobenzene, m-aminophenol, α-naphthol, resorcinol or 3-amino-6-methylphenol.

The total amount of the developer-coupler substance combination contained in the hair dye composition described here should be from about 0.1 to 8 percent by weight, advantageously from about 0.5 to 4 percent by weight.

The developer substances and coupler substances are generally used in equimolar amounts. It is however not disadvantageous when either the coupler or developer substances is used in excess with respect to the other.

According to the desired shade or tone for the dyed hair color one or more direct-dyeing hair dye compounds, especially nitro dye compounds, such as 4-amino-3-nitrophenol, 2-amino-6-chloro-4-nitrophenol, 1-hydroxy-2-(2'-hydroxyethyl)amino-4, 6-dinitrobenzene, 1-amino-2-nitro-4-(2'-hydroxyethyl)-amino-5-chlorobenzene and/or 4-(3'-hydroxypropyl)amino-3-nitrophenol.

The hair dye composition according to the invention can contain these hair dye compounds in an amount of from about 0.1 to 4 percent by weight. The total amount of these hair dye compounds and the combination of the developer substances and the coupler substances in the hair dyeing composition according to the invention amounts to from about 0.1 to 8 percent by weight, advantageously from 0.5 to 5 percent by weight.

The oxygen-oxidoreductase/substrate system used in the hair dye composition according to the invention facilitates oxidation of the developer/coupler substance combination by oxygen present in the air or air oxygen without addition of hydrogen peroxide. The following oxygen-oxidoreductase/substrate systems are particularly preferred:

glucose-oxidase (EC 1.1.3.4)/D-glucose
alcohol-oxidase (EC 1.1.3.13)/ethanol
pyruvate-oxidase (EC 1.2.3.3)/pyruvate
oxalate-oxidase (EC 1.2.3.4)/oxalate
cholesterol-oxidase (EC 1.1.3.6)/cholesterol
uricase (EC 1.7.3.3)/urea
lactate-oxidase/lactic acid
xanthine-oxidase (EC 1.1.3.22)/xanthine.

The use of the glucose-oxidase/D-glucose system, in which hydrogen peroxide is formed from air oxygen and water in situ, in combination with peroxidase (EC 1.11.1.7) is particularly preferred. Both the glucose-oxidase and the peroxidase are advantageously catalase free (glucose-oxidase:catalase activity <1% of the total glucose-oxidase activity; peroxidase:catalase activity <0.5% of the total peroxidase activity).

The amount of oxidoreductase and/or peroxidase depends on the purity of the enzymes used. This usually amounts to from 50 to 20,000 units per 100 g dye composition, advantageously from 100 to 1000 units per 100 g dye composition, for the oxidoreductase—referenced to the activity determining system (e.g. for the glucose oxidase: glucose/guaiacol/O2 saturated; pH=7; at 25° C.). For the peroxidase it amounts to from 50 to 20000 units per 100 g of dye composition, advantageously from 100 to 1000 units per 100 g of dye composition,—referenced to the activity determining system (guaiacol/H$_2$O$_2$; pH=7; 25° C.)

The amount of the substrate in the composition according to the invention may be from 0.5 to 25 percent by weight, advantageously from 1 to 15 percent by weight.

Moreover standard cosmetic additives, such as perfume oil, preservative substances, complex formers, thickeners or hair care materials, may be contained in the composition according to the invention.

The form of the new hair dye composition can, e.g., be a solution, especially an aqueous or aqueous-alcoholic solution, a cream, a gel or an emulsion. It can include a mixture of hair dye compounds with the enzyme substrate system and the standard additives used in this type of preparation.

The standard cosmetic additives for the solutions, creams, emulsions or gels according to the invention are, for example, solvents, such as water, lower aliphatic alcohols, e.g. ethanol, propanol or isopropanol, glycerol, glycol ether or glycols, such as 1,2-propylene glycol, additional wetting agents or emulsifiers from the classes of anionic, cationic, amphoteric or nonionic surfactants, e.g. fatty alcohol sulfates, ethoxylated fatty alcohol sulfates, alkylsulfonates, alkylbenzene sulfonates, alkyltrimethyl ammonium salts, alkylbetaines, ethoxylated fatty alcohols, ethoxylated nonylphenols, fatty acid alkanolamides, ethoxylated fatty acid esters; thickeners, such as higher fatty alcohols, starches, cellulose derivatives, petrolatum, paraffin oils and fatty acids; and hair care substances, such as cationic resins, lanolin derivatives, cholesterol, pantothenic acid and betaine. The above-mentioned ingredients are used in standard amounts suitable for their purposes. For example, the wetting agents and emulsifiers are used in concentrations of about 0.5 to 30 percent by weight, the thickeners are used in amounts of from about 0.1 to 25 percent by weight and the hair care substances are used in concentrations of about 0.1 to 5.0 percent by weight.

The addition of nonionic surfactants—especially fatty alcohol polyglycol ethers of formula II

wherein R represents an alkyl group having from 1 to 20 carbon atoms and n represents a whole number from 2 to 20—in amounts of from 0.1 to 10 percent by weight.

The hair dyeing composition according to the invention can also contain an acid or a base and a buffer system for adjustment of the pH value. Alkanolamines, alkylamines, alkali metal hydroxides and ammonium hydroxide or alkali carbonates and ammonium carbonate may be used as the base or alkalizing agent. Organic or inorganic acids, such as lactic acid, acetic acid, tartaric acid, citric acid, ascorbic acid, boric acid, nitric acid or phosphoric acid can be used as the acid. A citrate buffer, a phosphate buffer or a borate buffer may be used as a suitable buffer system. The borate buffer(boric acid/NaOH) and the phosphate buffer(KH$_2$PO$_4$/K$_2$HPO$_4$) in the pH range of 6 to 9.5 are particularly preferred in the composition according to the invention.

Furthermore the composition according to the invention can be in the form of an aerosol preparation, e.g. an aerosol foam, or in the form of a dye powder or dye granulate. The dye powder or dye granulate is a mixture of the lyophilized enzyme with the remaining powdery and other ingredients which are as water-free as possible. Next it is mixed directly with water or a water/alcohol mixture to make the ready-to-use dye preparation for dyeing hair.

It is also possible to make the composition according to the invention as a multi-component preparation. Thus, e.g., the ready-to-use preparation can be made immediately prior to use by mixing of two components, in which the first component is made from one or more enzymes (advantageously in lyophilized form), while the second component includes the remaining ingredients of the hair dye composition.

Furthermore it is possible to use a composition according to the invention in the form of a three-component preparation. In this three component preparation the first component includes one or more enzymes (advantageously in lyophilized form), while the second component comprises a mixture of the remaining powdery ingredients and the third component comprises water or a water/alcohol mixture.

Alternatively the enzyme can be packaged in the form of a one component preparation, also in microencapsulated form.

In the method of dyeing hair using the hair dye composition according to the invention an amount of the ready-to-use hair dye composition according to the invention sufficient for dyeing hair, according to the amount of the hair from about 60 to 200 g, is applied to the hair.

In the method of dyeing hair according to the invention the hair dye composition according to the invention is allowed to act on the hair for about 15 to 60 minutes, advantageously from 25 to 55 minutes, according to the desired color intensity or depth for the dyed hair at 15° to 50° C. and then the hair dye composition is rinsed from the hair with water and the hair is dried. If necessary the hair can be washed with a shampoo in connection with this rinsing. Subsequently the hair is then dried.

The action of the hair dye composition according to the invention can be clearly shortened when the hair dye composition according to the invention is dispensed from an air-tight container(e.g. an aerosol case) and prior to dispensing is subjected to a pre-oxidation with air oxygen with stirring for 15 to 60 minutes.

The composition according to the invention for dyeing keratin fibers is especially suitable for dyeing human hair and allows a very protective and most intensive dyeing of the hair. Particularly by addition of suitable direct-dyeing hair dyes also very dark natural shades or color can be obtained.

The following examples serve to illustrate the subject matter of the claimed invention but should not be interpreted as limiting the scope of the claims appended hereinbelow.

EXAMPLES

Examples 1a to 1d. Hair Dye Composition

| | | |
|---|---|---|
| 0.0025 | mol | developer substance |
| 0.0025 | mol | coupler substance of formula I |
| 400 | units | glucose oxidase (EC 1.1.3.4) |
| 400 | units | peroxidase (EC 1.11.1.7) |
| 5.0 | g | isopropanol |
| 2.0 | g | 1,2-propandiol |
| 1.4 | g | polyethyleneglycol(20)stearyl ether |
| 1.0 | g | glycerol |
| 1.0 | g | D-glucose |
| 0.3 | g | disodium ethylenediaminotetraacetate |
| 0.1 | g | ascorbic acid |
| — | | borate buffer (0.1 Molar) |
| ad 100.0 | g | |

The pH value of the hair dye composition is adjusted with sodium hydroxide until at a value of 7.7.

The hair dye composition is applied to bleached hair. After an acting time of 30 or 60 minutes at room temperature (20° to 25° C.) the hair is washed with lukewarm water and then dried.

The following Table I below shows the particular developer and coupler compounds used in the hair dye compositions of examples 1a to 1d and 2a to 2c(these individual compounds were not specified above).

TABLE I COUPLER AND DEVELOPER COMPOUNDS OF EXAMPLES 1a–1d

Example 1a,2a
Developer: hydroxyethyl-p-phenylenediamine sulfate
Coupler: 2-amino-4-(2'-hydroxyethyl)aminoanisole sulfate Example 1b,2b
Developer: 2,5-diaminotoluene sulfate
Coupler: 2-amino-4-(2'-hydoxyethyl)aminoanisole sulfate Example 1c,2c
Developer: 2,5-diaminotoluene sulfate
Coupler: 4-(2'-hydroxyethoxy)-1,3-diaminobenzene dihydrochloride Example 1d
Developer: 4-amino-m-cresol
Coupler: 2-amino-4-(2'-hydroxyethyl)aminoanisole sulfate Table II hereinbelow shows the color characteristics or properties of hair dyed with the compositions of examples 1a to 1d for an acting time of 30 minutes as well as an acting time of 60 minutes. The color characteristics for the dyed hair were measured by a Minolta calorimeter, Type Chromameter II. The L in Table II indicates the color intensity or brightness and ranges from 0 to 100(a pure white would correspond to L=100). The smaller the L value, the more intense or the deeper the color.

The a and b values characterize the tone or shade of the color of the dyed hair. The a-value in the Table II below is a measure of the red tones in the color (the greater this value, the more intense are these red tones). The b-value is a measure of the yellow tones(the yellow tones are greater as the b value increases).

Exemplary compositions 1a to 1c dye hair a deep blue color while composition 1d dyes hair purple-red.

TABLE II

COLOR CHARACTERISTICS FOR HAIR DYED WITH EXEMPLARY COMPOSITIONS 1a to 1d

| Example | Acting time | L | a | b |
|---|---|---|---|---|
| 1a | 30 m | 35.22 | 3.85 | −14.13 |
| 1a | 60 m | 25.08 | 4.94 | −12.42 |
| 1b | 30 m | 30.94 | 4.06 | −13.94 |
| 1b | 60 m | 24.10 | 4.54 | −12.74 |
| 1c | 30 m | 32.67 | 3.55 | −15.85 |
| 1c | 60 m | 23.73 | 4.47 | −13.42 |
| 1d | 30 m | 35.58 | 20.41 | −0.03 |
| 1d | 60 m | 27.80 | 18.02 | −0.11 |

Examples 2a to 2d. Hair Dye Composition

| | | |
|---|---|---|
| 0.0025 | mol | developer substance |
| 0.0025 | mol | coupler substance of formula I |
| 400 | units | glucose oxidase (EC 1.1.3.4) |
| 400 | units | peroxidase (EC 1.11.1.7) |
| 5.000 | g | isopropanol |
| 2.000 | g | 1,2-propandiol |
| 1.400 | g | polyethyleneglycol(20)stearyl ether |
| 1.000 | g | glycerol |
| 1.000 | g | D-glucose |
| 0.300 | g | disodium ethylenediaminotetraacetate |
| 0.100 | g | ascorbic acid |
| 0.075 | g | 2-amino-6-chloro-4-nitrophenol |
| — | | borate buffer (0.1 Molar) |
| ad 100.0 | g | |

The pH value of the hair dye composition is adjusted with sodium hydroxide until at a value of 7.7.

The hair dye composition is applied to bleached hair. After an acting time of 30 or 60 minutes at room temperature (20° to 25° C.) the hair is washed with lukewarm water and then dried.

The particular developer and coupler compounds used in the hair dye compositions of examples 2a to 2c are the same as the selected developers and couplers of examples 1a to 1c respectively.

Table III hereinbelow shows the color characteristics or properties of hair dyed with the compositions of examples 2a to 2c as measured by a calorimeter for an acting time of 30 minutes as well as an acting time of 60 minutes. The values L, a and b have the same significance as described hereinabove.

Exemplary compositions 2a to 2c dye hair a brown.

TABLE III

COLOR CHARACTERISTICS FOR HAIR DYED WITH EXEMPLARY COMPOSITIONS 2a to 2c

| Example | Acting time | L | a | b |
|---|---|---|---|---|
| 2a | 30 m | 32.57 | 0.67 | 4.71 |
| 2a | 60 m | 25.54 | 0.89 | 3.97 |
| 2b | 30 m | 31.11 | 0.24 | 2.67 |
| 2b | 60 m | 23.65 | 0.84 | 0.88 |

TABLE III-continued

COLOR CHARACTERISTICS FOR HAIR DYED WITH
EXEMPLARY COMPOSITIONS 2a to 2c

| Example | Acting time | L | a | b |
|---|---|---|---|---|
| 2c | 30 m | 29.14 | −0.26 | 1.89 |
| 2c | 60 m | 21.24 | 0.46 | −0.40 |

Example 3. Hair Dye Powder Composition

| | | |
|---|---|---|
| 0.520 | g | 2-amino-4-(2'-hydroxyethyl)amino-anisole sulfate |
| 0.310 | g | 4-amino-3-methylphenol |
| 0.080 | g | 4-amino-2-hydroxytoluene |
| 0.075 | g | 2-amino-6-chloro-4-nitrophenol |
| 400 | units | glucose oxidase (EC 1.1.3.4) |
| 400 | units | peroxidase (EC 1.11.1.7) |
| 1.000 | g | D-glucose |
| 0.400 | g | sodium hydroxide |
| 0.350 | g | hydroxethylcellulose |
| 0.300 | g | disodium ethylenediaminotetraacetate |
| 0.100 | g | ascorbic acid |
| 0.280 | g | boric acid |

The powder described above is mixed with water with shaking or stirring to make 100 g of a hair dye mixture.

The hair dye mixture so obtained is applied to bleached hair. After an acting time of 30 minutes at room temperature (20°–25° C.) the hair is washed with lukewarm water and dried. The dyed hair has an intense copper color.

Example 4. Two-component Hair Dye Composition

Component A:

| | | |
|---|---|---|
| 0.0025 | mol | 2,5-diaminotoluene sulfate |
| 0.0025 | mol | 2-amino-4-(2'-hydroxyethyl)amino-anisole sulfate |
| 5.000 | g | isopropanol |
| 2.000 | g | 1,2-propandiol |
| 1.400 | g | polyethyleneglycol(20)stearyl ether |
| 1.000 | g | glycerol |
| 1.000 | g | glucose |
| 0.300 | g | disodium ethylenediaminotetraacetate |
| 0.100 | g | ascorbic acid |
| 0.075 | g | 2-amino-6-chloro-4-nitrophenol |
| — | | borate buffer (0.1 Molar) |
| ad 100.0 | g | |

Component B:

| | | |
|---|---|---|
| 400 | units | glucose oxidase (EC 1.1.3.4) |
| 400 | units | peroxidase (EC 1.11.1.7) |

Components A and B were mixed immediately prior to use and the pH value of the resulting hair dye mixture was adjusted with sodium hydroxide until at a value of 7.7.

The resulting hair dye mixture is applied in the same way as in example 1 but the acting time is 30 minutes.

The dyed hair is an intense brown color.

Unless otherwise noted, percentages are percentages by weight.

The information in parentheses following the enzyme name is the classification according to "Classification of International Union of Biochemistry on Nomenclature and Classification of Enzymes (1984)". The enzyme concentrations are given in the present application in "units"—the international unit proposed by the International Union of Biochemistry as the standard unit for all enzymes.

The disclosure of German Patent Application 196 10 392.4 of Mar. 16, 1996 is incorporated hereby reference.

This German Patent Application describes the same invention as described above and claimed in the claims appended hereinbelow and provides the basis for a claim of priority for the instant invention under 35 U.S.C. 119.

While the invention has been illustrated and described as embodied in an oxidation hair dye composition and method of dyeing hair using it, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A composition for oxidative dyeing of keratin fibers having a pH of from 6 to 9.5 and containing a combination of developer substance and coupler substance, an oxygen-oxido-reductase/substrate system and a peroxidase; wherein the coupler substance comprises a substituted m-phenylenediamine of formula I,

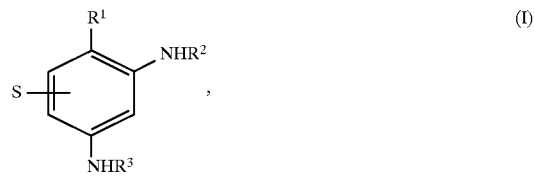

wherein $R^1$ is selected from the group consisting of alkoxy groups having from one to six carbon atoms, unsubstituted alkyl groups having from one to six carbon atoms and substituted alkyl groups having from one to six carbon atoms and at least one substituent, wherein said at least one substituent is selected from the group consisting of a hydroxy group, halogen atoms and $C_1$- to $C_6$-alkoxy groups, $R^2$, $R^3$ represent, independently of each other, hydrogen, another unsubstituted alkyl group having from one to six carbon atoms or another substituted alkyl group having from one to six carbon atoms and one or more hydroxy group, halogen atom or $C_1$- to $C_6$-alkoxy group substituents, and S represents a hydrogen atom or a further unsubstituted alkyl group having from one to six carbon atoms; or a physiologically compatible salt of the m-phenylenediamine of the formula (I).

2. A composition for oxidative dyeing of keratin fibers, said composition having a pH of from 6 to 9.5 and containing a combination of developer substance and coupler substance, an oxygen-oxido-reductase/substrate system and a peroxidase; wherein the coupler substance comprises at least one substituted m-phenylenediamine selected from the group consisting of
4-(2'-hydroxyethyl)-1,3-diaminobenzene dihydrochloride,
4-propyl-1,3-diaminobenzene dihydrochloride,
4-(2',2',2'-trifluoroethoxy)-1,3-diaminobenzene,
4-(2'-hydroxyethoxy)-1,3-diaminobenzene dihydrochloride,
2-amino-4-methoxyethylaminoanisole,
2-amino-4-hydroxypropylaminoanisole dihydrochloride,
2-amino-4-(2',2',2'-trifluoroethyl)aminoanisole,
4-amino-2-ethylaminoanisole dihydrochloride,
4-amino-2-(2',2',2'-trifluoroethyl)aminoanisole and
2-amino-4-(2'-hydroxyethyl)aminoanisole sulfate.

3. The composition for oxidative dyeing of keratin fibers as defined in claim 1, wherein the developer substance is selected from the group consisting of 1,4-diaminobenzene, 2,5-diaminotoluene, 2,5-diaminophenylethanol, o-aminophenol and 4-amino-m-cresol.

4. The composition for oxidative dyeing of keratin fibers as defined in claim 1, wherein a total amount of the combination of the developer substance and the coupler substance present is from about 0.1 to 8 percent by weight.

5. The composition for oxidative dyeing of keratin fibers as defined in claim 1, wherein said oxygen-oxidoreductase/substrate system is selected from the group consisting of glucose-oxidase(EC 1.1.3.4)/D-glucose, alcohol-oxidase (EC 1.1.3.13)/ethanol, pyruvate-oxidase(EC 1.2.3.3)/pyruvate, oxalate-oxidase(EC 1.2.3.4)/oxalate, cholesterol-oxidase(EC 1.1.3.6)/cholesterol, uricase(EC 1.7.3.3)/urea, lactate-oxidase/lactic acid and xanthine-oxidase (EC 1.1.3.22)/xanthine.

6. The composition for oxidative dyeing of keratin fibers as defined in claim 1, wherein said oxygen-oxidoreductase/substrate system comprises an oxygen-oxidoreductase and an substrate and said oxygen-oxidoreductase and said peroxidase each is present in an amount of from 50 to 20,000 units per 100 g dye composition.

7. The composition for oxidative dyeing of keratin fibers as defined in claim 6, containing from 0.5 to 25% by weight of said substrate.

8. The composition for oxidative dyeing of keratin fibers as defined in claim 1, further comprising at least one direct-dyeing hair dye compound selected from the group consisting of 4-amino-3-nitrophenol, 2-amino-6-chloro-4-nitrophenol, 1-hydroxy-2-(2'-hydroxyethyl)amino-4,6-dinitrobenezene, 1-amino-2-nitro-4-(2'-hydroxyethyl) amino-5-chlorobenzene and 4-(3'-hydroxypropyl)amino-3-nitrophenol.

9. The composition for oxidative dyeing of keratin fibers as defined in claim 1, further comprising from 0.1 to 10 percent by weight of a fatty alcohol polyglycol ether of formula II

R—O(CH$_2$—CH$_2$—O)$_n$—H        (II), wherein R represents an alkyl group having from 1 to 20 carbon atoms and n represents a whole number from 2 to 20.

10. The composition for oxidative dyeing of keratin fibers as defined in claim 1, further comprising a buffer selected from the group consisting of a citrate buffer, a phosphate buffer and a borate buffer.

11. The composition for oxidative dyeing of keratin fibers as defined in claim 1, in the form of an aqueous solution, an aqueous-alcoholic solution, a cream, a gel, an emulsion, an aerosol foam, a powder or a granulate.

12. The composition for oxidative dyeing of keratin fibers as defined in claim 1, in the form of a multicomponent preparation.

13. A method for the oxidative dyeing of hair, said method comprising the steps of:

a) providing a hair dye composition having a pH of from 6 to 9.5 and containing a combination of developer substance and coupler substance, an oxygen-oxidoreductase/substrate system and a peroxidase; wherein the coupler substance comprises a substituted m-phenylenediamine of formula I,

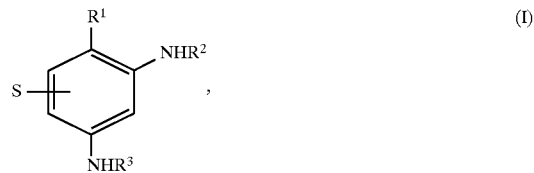

wherein $R^1$ is selected from the group consisting of alkoxy groups having from one to six carbon atoms, unsubstituted alkyl groups having from one to six carbon atoms and substituted alkyl groups having from one to six carbon atoms and at least one substituent, wherein said at least one substituent is a hydroxy group, a halogen atom or a $C_1$- to $C_6$-alkoxy group, $R^2$, $R^3$ represent, independently of each other, hydrogen, another unsubstituted alkyl group having from one to six carbon atoms or another substituted alkyl group having from one to six carbon atoms and one or more hydroxy group, halogen atom or $C_1$- to $C_6$-alkoxy group substituents and S represents a hydrogen atom or a further alkyl group having from one to six carbon atoms, or a physiologically compatible salt of the m-phenylenediamine of the formula (I);

b) applying from 60 to 200 g of the hair dye composition provided in step a) to the hair;

c) allowing the hair dye composition applied to the hair in step b) to act on the hair for 15 to 60 minutes at 15° to 50° C.; and d) rinsing the hair with water and drying the hair.

14. The method for the oxidative dyeing of hair as defined in claim 13, said method further comprising preparing the hair dye composition by mixing a hair dye powder or granulate with water.

* * * * *